(12) United States Patent
Alvarado (10) Patent No.: US 7,942,886 B2
(45) Date of Patent: May 17, 2011

(54) TRANSABDOMINAL NEEDLE INTRODUCER

(76) Inventor: Alfredo Alvarado, Weston, FL (US)

( * ) Notice: Subject to any disclaimer, the term of this patent is extended or adjusted under 35 U.S.C. 154(b) by 500 days.

(21) Appl. No.: 12/145,875

(22) Filed: Jun. 25, 2008

(65) Prior Publication Data

US 2009/0326566 A1    Dec. 31, 2009

(51) Int. Cl.
*A61B 17/04* (2006.01)
*A61F 2/02* (2006.01)

(52) U.S. Cl. ........ 606/144; 606/148; 606/139; 606/151; 623/23.72

(58) Field of Classification Search .................. 606/144, 606/148, 139, 151; 623/23.72
See application file for complete search history.

(56) References Cited

U.S. PATENT DOCUMENTS

| | | | |
|---|---|---|---|
| 5,281,237 A | 1/1994 | Gimpelson | |
| 5,336,239 A | 8/1994 | Gimpelson | |
| 5,507,755 A | 4/1996 | Gresl et al. | |
| 5,772,672 A | 6/1998 | Toy et al. | |
| 5,964,773 A | 10/1999 | Greenstein | |
| 6,383,201 B1* | 5/2002 | Dong | 606/151 |
| 6,755,868 B2* | 6/2004 | Rousseau | 623/23.64 |
| 6,966,916 B2* | 11/2005 | Kumar | 606/144 |
| 6,997,932 B2 | 2/2006 | Dreyfuss et al. | |

* cited by examiner

*Primary Examiner* — Vy Q Bui
(74) *Attorney, Agent, or Firm* — Mark D. Bowen, Esq.; Malin Haley DiMaggio Bowen & Lhota, P.A.

(57) ABSTRACT

A transabdominal needle introducer for the repair of large ventral incisional hernias comprises a handle connected to a long tubular shaft and a disposable needle cartridge at its distal end. The handle has a round knob or head, and a needle pusher to extrude the needles out. The long tubular shaft contains two metal rods disposed inside thereof, one to change the angle of the cartridge, and the other one to extrude the needles. At the proximal end of the tubular shaft there is a rotatable cylindrical control provided with a spiral groove that moves a metal rod destined to pivot the needle cartridge. The second metal rod inside the shaft is assigned to extrude the needles and is connected to a flexible resilient wire that protrudes at the distal end of the tubular shaft and is provided at its distal end with an oval tip that engages a piston-type pusher inside the needle cartridge. There are two straight needles inside the cartridge that are attached to a single strand of suture at each end, and they can be extruded by action of the needle pusher.

4 Claims, 7 Drawing Sheets

TRANSABDOMINAL NEEDLE INTRODUCER

CROSS REFERENCE TO RELATED APPLICATIONS

N/A

STATEMENT REGARDING FEDERALLY SPONSORED RESEARCH OR DEVELOPMENT

N/A

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office patent file or records, but otherwise reserves all copyrights rights whatsoever.

BACKGROUND OF THE INVENTION

1. Field of the Invention

The present invention relates to a new transabdominal needle introducer for the fixation of hernial mesh prosthesis used in the repair of abdominal wall hernias, more particularly incisional ventral hernias.

2. Description of Related Art

Surgically implanted mesh prosthesis have been used over the years for repair of abdominal wall hernias especially for the repair of incisional ventral hernias. This repair can be done by an open external technique or by an internal technique using laparoscopic instruments. The open technique requires dissection of the hernial sac and adjacent tissues in order to insert and secure the prosthesis in place. With this technique the patch can be inserted into the preperitoneal space behind the abdominal muscles, or intraperitoneally behind the peritoneal layer. In both techniques the prosthesis can be secured in place with full thickness transabdominal sutures, or with staples, or with spiral tacks. However the insertion of sutures to fix the prosthesis to the abdominal wall is time consuming and requires special suture passers. Furthermore, these sutures may produce persistent pain at the insertion sites. On the other hand the insertion of staples or spiral tacks using laparoscopic techniques, although less time demanding, may not hold as well as the transabdominal sutures. The use of full thickness transabdominal wall sutures give better results in terms of secure fixation but require more dexterity and proper orientation of the sutures which can add considerable time needed for the repair.

In the vast majority of cases, the implantable prosthesis consists of a composite patch made of a physical barrier to prevent formation of adhesions on the inner side, and knitted polypropylene monofilament mesh on the outer side to promote ingrowth and incorporation of the mesh into the abdominal wall.

Techniques Used for Hernial Prosthesis Fixation

Various methods has been used for the fixation of mesh prosthesis that include suture needles, suture passers, anchor sutures, and staples, clips or spiral tacks. Suture needles are difficult to insert due to the initial mobility of the patch and the difficult manipulation of the needles using laparoscopic techniques. Double needle sutures reduce the number of knots since they require one knot only for each pair of sutures. For example, U.S. Pat. No. 5,964,773, issued to Greenstein, discloses a suture needle holder and suture needle that includes a groove which leads to a blind hole to receive one end of a suture. The device with its wings retracted, is inserted down into the opening in the abdominal wall and the wings are pivoted to the open position. The shaft is withdrawn until the needles pierce the abdominal wall and protrude out of the wall. The suture is pulled out until it forms a loop beneath the opening. This device has been designed for closure of trocar holes and small holes of the abdominal wall and it is not intended for fixation of hernial patches.

Fixation of the prosthesis using suture passer devices require grasping and feeding of the suture into the grasping arm of the suture passer within the abdomen which is technically difficult and unwieldy. For instance, U.S. Pat. No. 5,772,672, issued to Toy, discloses an endoscopic suture passer for securing tissue within a body cavity using sutures but this device passes only one suture at a time which is time consuming. Similarly, U.S. Pat. No. 5,281,237, issued to Gimpelson, describes a surgical stitching device that allows a surgeon to place a "through and through" suture that passes only one suture a time. U.S. Pat. No. 6,997,932, issued to Dreyfuss, describes a suture passer provided with two curved needles for closure of puncture wounds. This device is unable to pass the needles through the whole layers of the abdominal wall because the size and shape of the needles.

Anchor sutures comprise an anchor attached to a suture that is passed in pairs to fix a hernial patch in place. The sutures are tied together beneath the skin which represents superior comfort to the patient. However, this method requires the insertion of individual sutures which is time consuming and cumbersome. For instance U.S. Pat. No. 6,966,916, issued to Kumar, describes a surgical opening repair device that comprises a hollow tube into which an anchor attached to a suture is inserted. The hollow tube, which includes a stylet to maneuver the anchor inside, is inserted through the edges of the wound and into the edges of the patch, and then removed allowing the anchor to hold the patch in place. A similar maneuver is made to insert a second anchor suture and the free ends of both sutures are tied together forming a holding suture. An obvious difficulty is evident when attempting to pierce the edges of the patch with a hollow tube of large diameter as described in this patent. U.S. Pat. No. 5,507,755, issued to Gresl et al. describes an apparatus for suturing deep puncture wounds that includes suture-carrying needles with anchors attached. The suture-carrying needles are individually passed through the tissue layers around the wound and subsequently passed through a capturing membrane. The anchors become engaged by the membrane and then pulled out bringing the ends of the suture out of the wound. This particular apparatus seems to be too complicated and not very practical.

U.S. Pat. No. 5,336,239, issued to Gimpelson, describes a surgical needle for use in narrow, deep incisions in the abdominal wall. The needle has an elongated shaft with a proximally directed hook at its distal end and the hook has an eye adjacent to its point through which a suture can be threaded. The hook is inserted through the incision and manipulated to place the suture "through and through" a selected portion of the abdominal wall.

In summary, full thickness transabdominal sutures offer the best results in terms of avoiding recurrences because tacks and staples do not penetrate deeply enough to fix the mesh into the peritoneal layer. The problem is that transabdominal sutures require more time for proper patch fixation.

BRIEF SUMMARY OF THE INVENTION

The present invention overcomes the limitations and disadvantages present in the art by providing a novel transabdominal needle introducer for the repair of large ventral incisional hernias. This device comprises a handle connected to a long tubular shaft and a disposable needle cartridge at its distal end. The handle has a round knob or head, and a needle pusher to extrude the needles out. The long tubular shaft contains two metal rods disposed inside thereof one to change the angle of the cartridge, and the other one to extrude the needles. At the proximal end of the tubular shaft there is a rotatable cylindrical control provided with a spiral groove that moves a metal rod destined to pivot the needle cartridge. The second metal rod inside the shaft is assigned to extrude the needles and is connected to a flexible resilient wire that protrudes at the distal end of the tubular shaft and is provided at its distal end with an oval tip that engages a piston-type pusher inside the needle cartridge. There are two straight needles inside the cartridge that are attached to a single strand of suture at each end, and they can be extruded by action of the needle pusher.

Accordingly, it is the object of the present invention to provide a needle introducer that inserts two straight needles through the whole layers of the abdominal wall from inside out.

Another object of the invention is to provide a needle introducer that can be inserted through a laparoscopic cannula into the abdominal cavity.

Still another object of the present invention is to speed up the process of inserting transabdominal sutures by using disposable needle cartridges.

In accordance with these and other objects, which will become apparent hereinafter, the instant invention will now be described with particular reference to the accompanying drawings.

BRIEF DESCRIPTION OF THE SEVERAL VIEWS OF THE DRAWINGS

FIG. 3 B is a transverse sectional view at the level A-A of FIG. 3A showing the walls of the needle cartridge with an empty needle guide inside displaying two square canals destined to keep the needles and suture in place.

FIG. 3 C is a transverse sectional view of the pivoting member of the needle introducer at the level B-B of FIG. 3A. showing a groove to accommodate the resilient flexible wire.

FIG. 3 D is a side view of the pivoting member of the same introducer.

DETAILED DESCRIPTION OF THE INVENTION

Figure 1A:
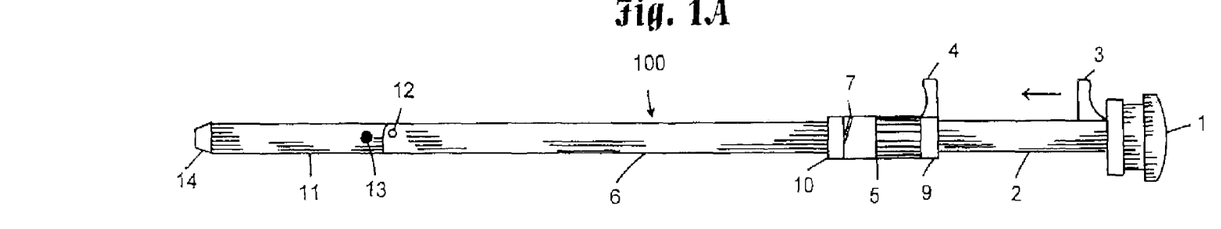
FIG. 1A is a side elevation of the transabdominal needle introducer in a straight position.
Figures 1B, 1C:
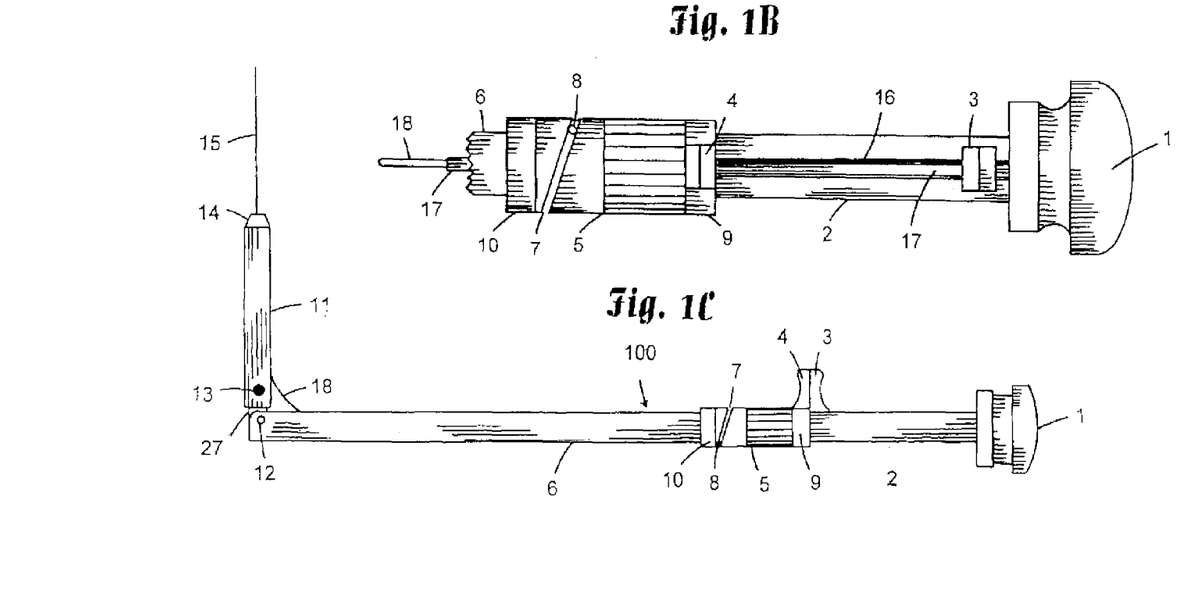
FIG. 1B is an enlarged fragmentary top view elevation of the same introducer showing, in more detail, the handle with its pushing rod and sliding slit, and also the cylindrical control knob.
FIG. 1C is a side elevation of the same introducer in an angulated position.

Referring to the drawing of FIG. 1A it shows the transabdominal needle introducer 100 in a straight position to make possible its introduction through a laparoscopic cannula (not depicted here). A handle knob 1 is coaxially attached to a sliding segment 2 containing a slidable pusher 3 which moves toward fixed stopper 4. The invention is provided with a rotatable cylindrical control 5 that encircles the proximal tubular shaft 6. Cylindrical control 5 has a spiral groove 7 that accommodates the angulated end 8 of a pivoting rod (not depicted here). Cylindrical control 5 is restricted between proximal restrictive collar 9 and distal restrictive collar 10. Cartridge 11 pivots on axis 12 and is secured in place by button-knob 13. There is needle guide 14 at the tip of cartridge 11. Referring to FIG. 1B three is depicted an enlarged top view of the proximal end of the invention showing the handle knob 1, the pusher segment 2, the slidable pusher 3 attached to pushing rod 17 that runs inside slit 16, the fixed stopper 4 attached to restrictive collar 9, and the cylindrical control 5 with its spiral groove 7 to accommodate angulated end 8 of a pivoting rod (not depicted here). The drawing also shows the distal restrictive collar 10, part of the tubular shaft 6, and the pushing rod 17 attached to resilient flexible wire 18. Referring to FIG. 1C there is depicted the transabdominal needle introducer 100 in an angulated position with needles 15 extruded through needle guide 14 after being pushed by action of slidable pusher 3 which has stopped at stopper 4.

Needles 5 has been extruded by action of resilient flexible wire 18. Cartridge 11 is snapped on pivoting member 27 and is secured in place by action of button knob 13. Pivoting member 27 moves on axis 12 and is activated by a pivoting rod (not shown here).

Figure 2A:
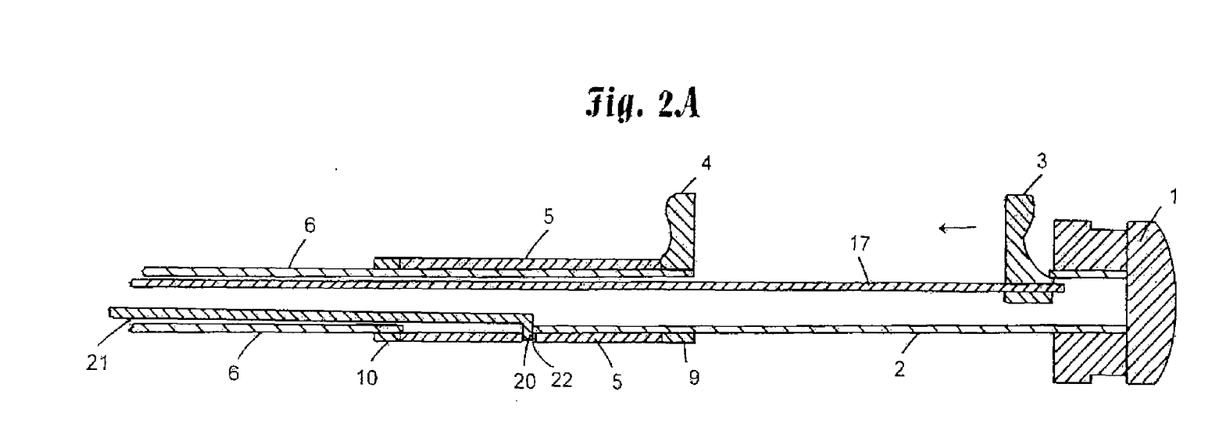
FIG. 2A is a fragmentary section side view of transabdominal needle introducer showing its proximal portion that includes the handle with the pusher mechanism and the pivoting rod.
Figures 2B, 2C:
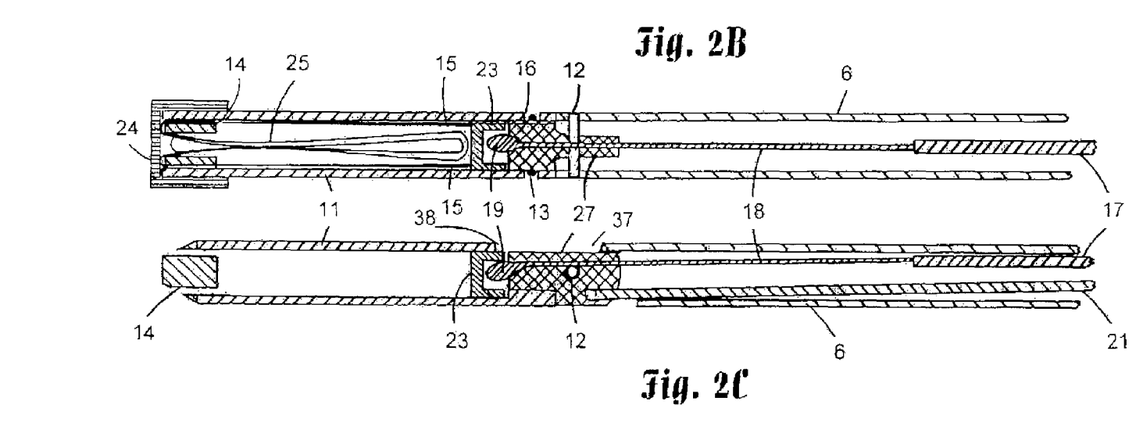
FIG. 2B is a fragmentary section top view of the distal portion of the transabdominal needle introducer showing the pivoting member of the shaft engaging the disposable needle cartridge which contains two straight needles and a single strand of suture.
FIG. 2C is a fragmentary section side view of the distal portion of the same introducer showing the pivoting member with a resilient flexible wire riding on top and engaging a piston-type pusher within the needle cartridge. (Needles and suture have been deleted for clarity).

Referring to FIG. 2A there is shown the proximal segment of the transabdominal needle introducer with a knob handle coaxially attached to sliding segment 2 that contains pusher rod 17 attached to pusher 3 that moves forward to be detained by stopper 4. Cylindrical control 5 has a spiral groove that engages angulated end 20 of pivoting rod 21 that moves backward and forward by action of cylindrical control 5 which rotates in between proximal collar 9 and distal collar 10. FIG. 2B shows the distal segment of the transabdominal needle introducer with pushing rod 17 attached at its distal end to resilient flexible wire 18 that runs on top of pivoting member 27. Olive head 19 at tip of resilient flexible wire 18 engages inside piston-type pusher 23 which moves forward inside cartridge 11 to push needles 15 that are attached to single thread 25. There is a needle guide 14 at the end of cartridge 11 that holds needles 15 and folded single suture 25 in place. The blunt end of each needle 15 is attached to a single strand suture 25 inside cartridge 11. Disposable cartridge 11 is provided with a protective cap 24. FIG. 2C is a sectional side view that shows pivoting rod 21 connected to pivoting member 27 which moves on axis 12. Resilient flexible wire 18 runs on a groove (not depicted here) on top of pivoting member 27 and ends with olive head 19 to engage piston-type pusher 23. Needle guide 14 is empty because needles 151 and suture 25 have been removed.

Figure 3A:
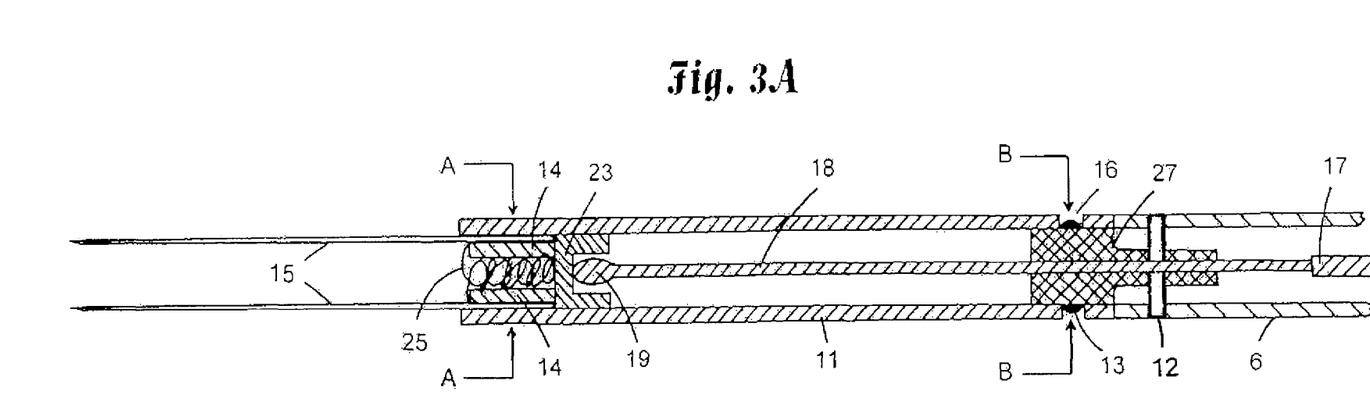
FIG. 3A is fragmentary section top view of the transabdominal needle introducer with two needles partially extruded by action of the piston-type pusher and the resilient flexible wire.
Figure 3B:
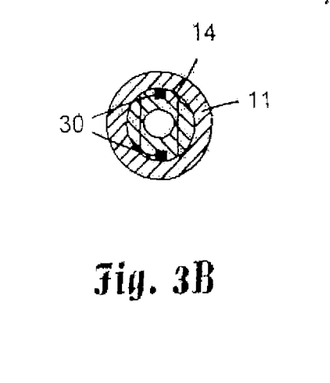
Figure 3C:
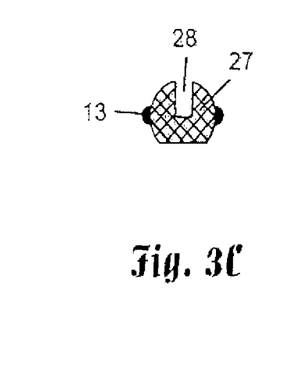
Figure 3D:
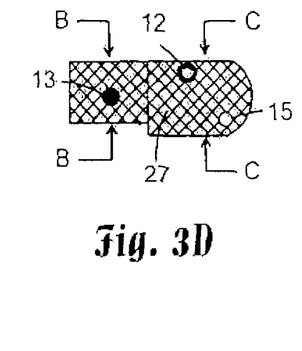
Figure 3E:
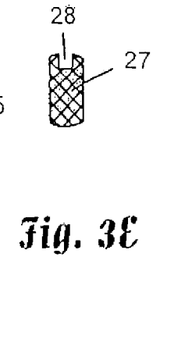
FIG. 3E is a transverse sectional view of the pivoting member of the same introducer at the level C-C of FIG. 3D showing a groove to accommodate the resilient flexible wire.

FIG. 3A is a longitudinal sectional view of needle cartridge 11 with two straight needles 15 attached to a thread 25 and partially extruded after being pushed by pusher piston 23. It also shows resilient flexible wire 18 connected to pushing rod 17 and engaged in piston-type pusher 23. Resilient flexible wire 18 is riding on pivoting member 27 which is connected to cartridge 11 by snapping button knob 13 in cartridge holes 16. FIG. 3B is a transverse sectional view of distal end of cartridge 11 at level A-A of FIG. 3A showing needle guide 14 with two square grooves 30 destined to keep needles 15 and thread 25 in place. FIG. 3C is a cross sectional view of pivoting member 27 at level B-B of FIG. 3A showing groove 28 destined to accommodate resilient flexible wire 18 (not shown here) and button knobs 13. FIG. 3D is a side view of pivoting member 27 with button knob 13 which engages with corresponding holes 16 in needle cartridge 11. This view also shows pivoting axis 12 and hole 15 for engaging angled end of pivoting rod 21. FIG. 3E is a cross sectional view of pivoting member 27 at level C-C of FIG. 3D showing a rather shallow groove 28 destined to accommodate resilient flexible wire 18 (not shown here).

Figure 4:
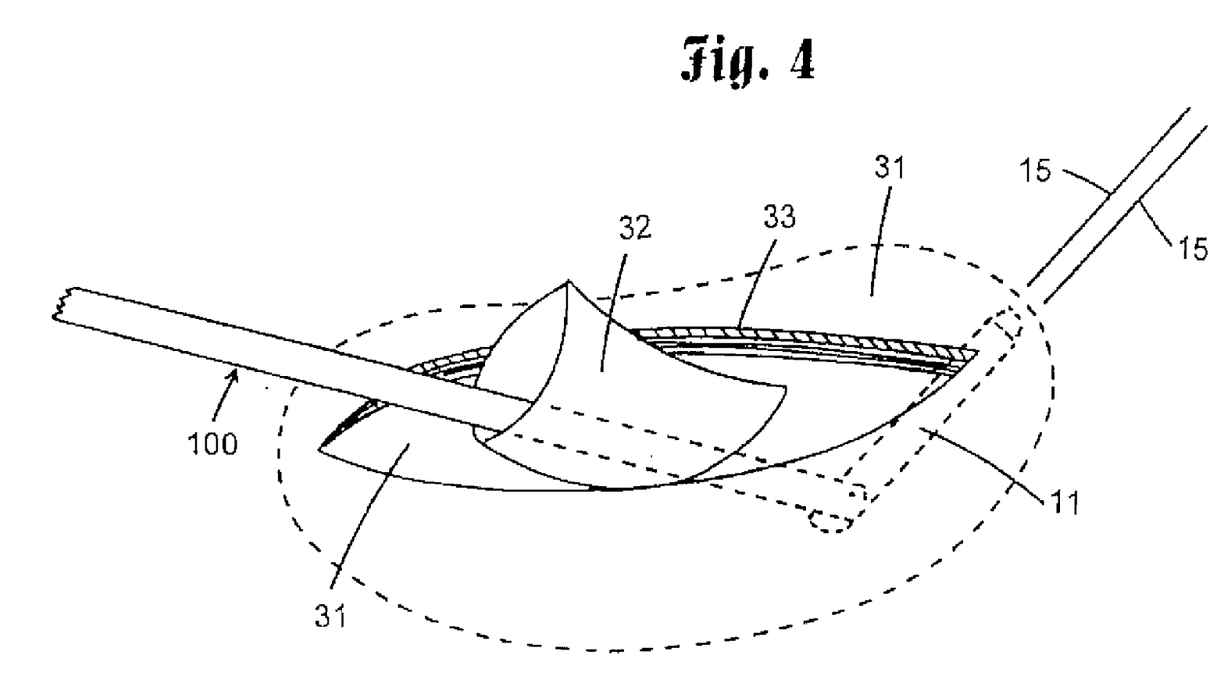
FIG. 4 shows the transabdominal needle introducer which has been inserted through the sleeve of a special hernial prosthesis for intraprosthetic fixation which has been placed inside the peritoneal cavity.

FIG. 4 is a diagrammatic representation of the transabdominal needle introducer 100 that has been inserted through sleeve 32 of a special prosthesis 31 for intraprosthetic fixation. In this drawing the cartridge 11 has been placed inside the prosthesis 31 and directed to one edge, and needles 15 are protruding through the abdominal wall 33.

Figure 5:
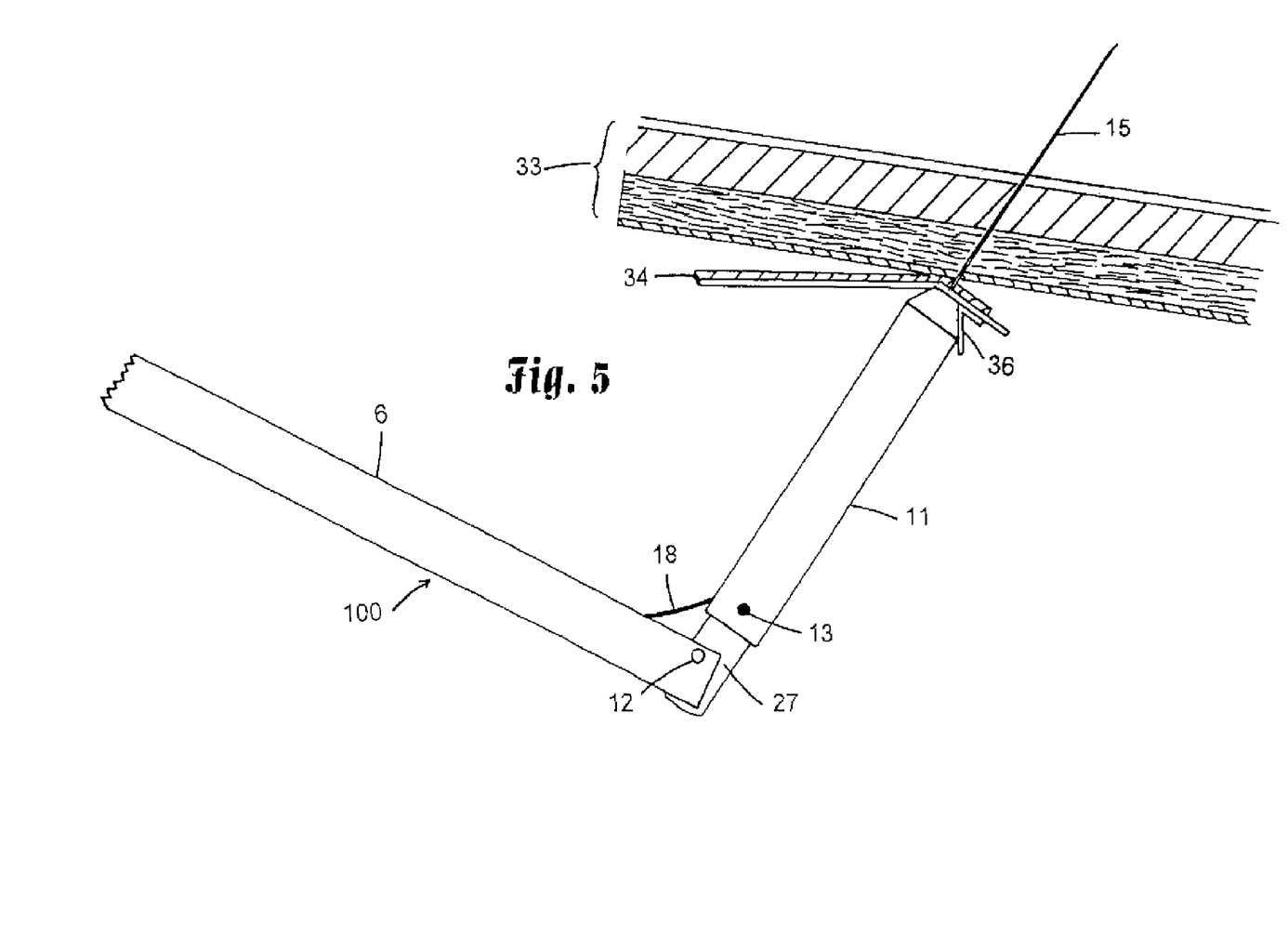
FIG. 5 is a diagrammatic view of the transabdominal needle introducer with a needle piercing through the edge of another special hernial prosthesis, provided with a bounding rim, and exiting through the abdominal wall.

FIG. 5 shows the device 100 which has been introduced laparoscopically into the abdominal cavity and then directed toward the abdominal wall layers 33 to engage the bounding rim 36 of a special composite prosthesis 34. Needles 15 have been inserted through prosthesis 34 and abdominal wall layers 33 to secure the prosthesis in place. This drawing also shows pivoting member 27 with its pivoting axis 12 and button knob 13 to hold needle cartridge 11 in place. Resilient flexible wire 18 is in a bending position 8 and jumps from tubular shaft 6 to needle cartridge 11.

Figure 6:
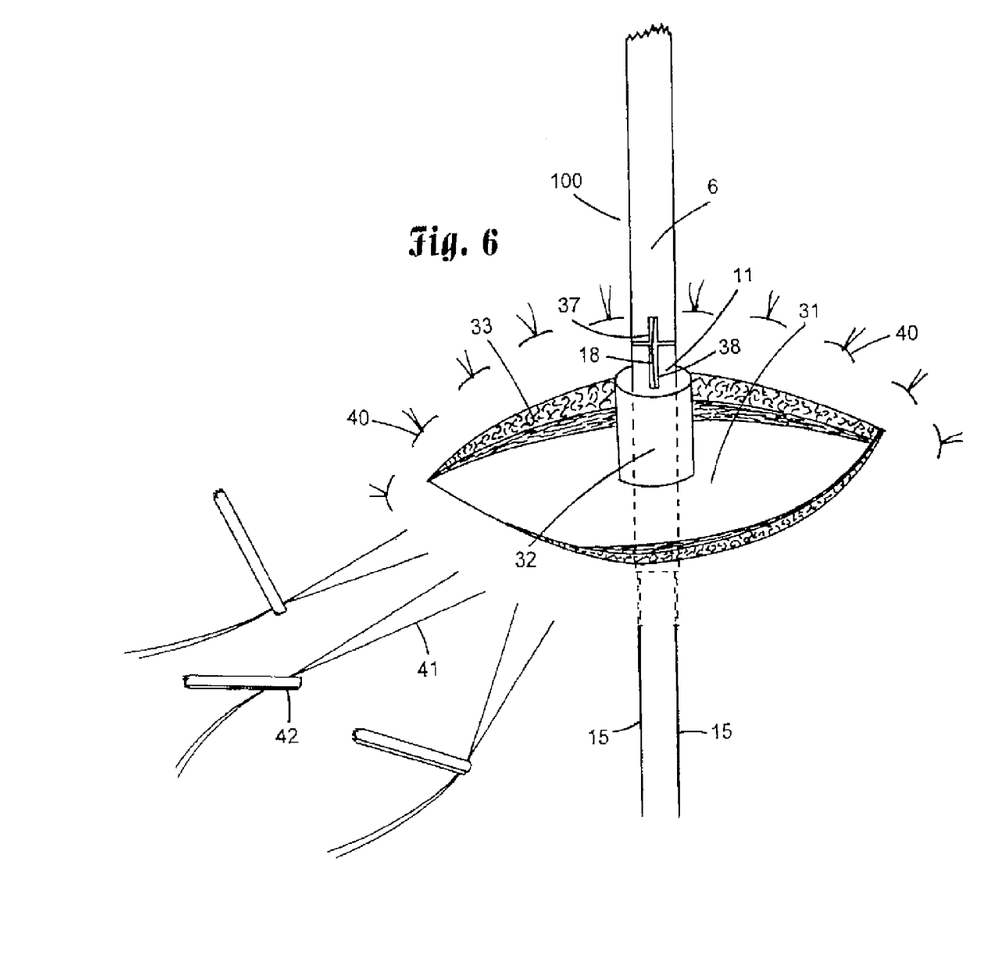
FIG. 6 is an elevation view of a transabdominal needle introducer which has been introduced into the sleeve of a special hernial prosthesis for intraprosthetic fixation showing the extrusion of two straight needles through the abdominal wall.

FIG. 6 is a perspective view showing a representative manner in which multiple sutures may be located at various positions at the edges of the prosthesis. In this drawing the transabdominal needle introducer 100 has been introduced through the sleeve 32 of a special prosthesis for intraprosthetic fixation and directed to one edge of the prosthesis. The needles 15 has been extruded through the abdominal wall 33 and ready to be pulled out. Several sutures 40 have been tied snugly and three more sutures 41 have been temporarily secured with hemostats 42.

Figure 7A:
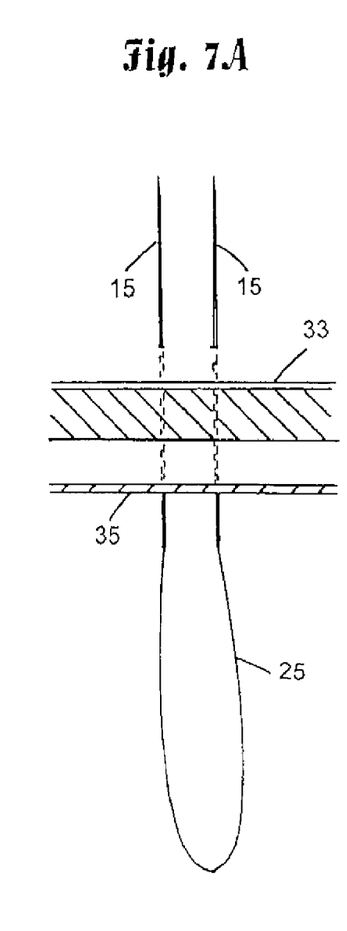
FIG. 7A is a diagrammatic sectional view of the abdominal wall and a single hernial mesh being pierced by two straight needles from inside out.
Figure 7B:
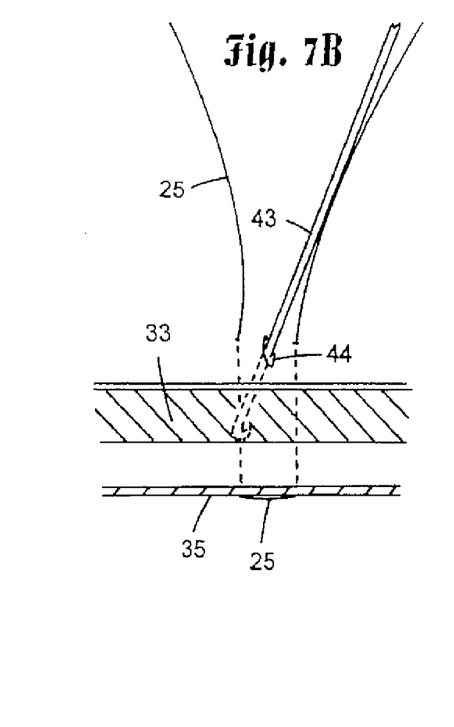
FIG. 7B shows a suture loop holding the mesh against the abdominal wall and one crochet needle retrieving one arm of the suture through a small stab wound.
Figure 7C:
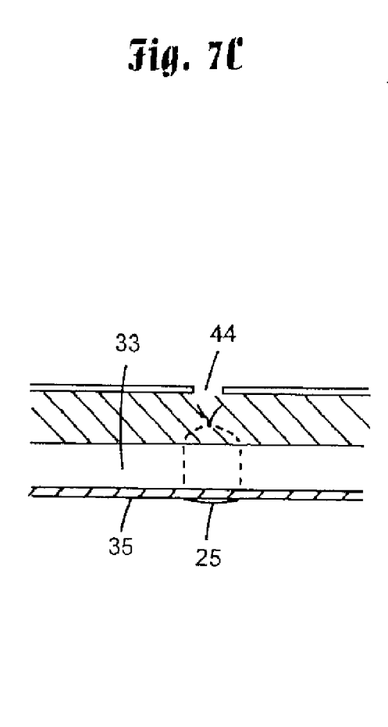
FIG. 7C shows the mesh fixed with a suture loop which has been tied through the stab wound under the skin.

FIG. 7A is a diagrammatic representation of two straight needles 15 being inserted through abdominal wall 33 and carrying a single strand suture 25 to affix surgical mesh 35 to abdominal wall 33. FIG. 7B shows the loop suture 25 holding the mesh against the abdominal wall 33, and a crochet needle 43 retrieving one arm of the suture through a small stab wound 44. FIG. 7C shows the loop suture 25 tied snugly under the skin through stab wound 44, to fix mesh 35 against the abdominal wall 33.

The instant invention has been shown and described herein in what is considered to be the most practical and preferred embodiment. It is recognized, however, that departures may be made therefrom within the scope of the invention and that obvious modifications will occur to a person skilled in the art.

What I claim is:

1. A transabdominal needle introducer for fixation of hernial prosthesis used in the repair of incisional ventral hernias, said transabdominal needle introducer comprising:
    a tubular shaft having a proximal end and a distal end;
    a sliding segment generally coaxially and adjacently disposed with said tubular shaft proximal end;
    a handle having a knob head coaxially attached to said sliding segment;
    said sliding segment defining a slit with a slidable pusher member at least partially received within said slit in slidable relation with said sliding segment, said slidable pusher member attached to a pusher rod, said pusher rod having a wire projecting from a distal end thereof;
    a rotatable cylindrical control disposed in concentric relation with said tubular shaft and rotatable relative thereto, said cylindrical control defining a longitudinal spiral groove;
    a pivoting rod having an angulated end received within said spiral groove, whereby rotation of said cylindrical control causes forward and backward movement of said pivoting rod relative to said tubular shaft;
    said tubular shaft distal end having a pivoting member connected thereto, said pivoting member pivoting relative to said tubular shaft upon forward and backward movement of said pivoting rod;
    a generally hollow disposable cartridge removably connected to said pivoting member, said cartridge including two straight surgical needles connected by thread and a piston-type pusher slidably disposed therein, said piston-type pusher movable by said wire in order to extrude said two straight surgical needles.

2. A trans abdominal needle introducer according to claim 1, further including a stop member for detaining said sliding segment.

3. A transabdominal needle introducer according to claim 1, wherein said rotatable cylindrical control rotates between two restrictive collars.

4. A transabdominal needle introducer according to claim 1, wherein said tubular shaft is connected to said pivoting member by means of a transverse pin that serves as an axis of said pivoting member to change the angle of the cartridge.

* * * * *